US006998271B2

(12) United States Patent
Wong et al.

(10) Patent No.: US 6,998,271 B2
(45) Date of Patent: Feb. 14, 2006

(54) LUMINESCENT SENSORY MATERIAL FOR ORGANIC-HALOGEN COMPOUNDS, AND METHODS AND APPARATUS UTILIZING SUCH

(75) Inventors: Kwok-Yin Wong, Hong Kong (CN); Chi-Ming Che, Hong Kong (CN); Wei Lu, Hong Kong (CN); Zhike He, Hong Kong (CN)

(73) Assignees: The Hong Kong Polytechnic University, Hong Kong (CN); The University of Hong Kong, Hong Kong (CN)

( * ) Notice: Subject to any disclaimer, the term of this patent is extended or adjusted under 35 U.S.C. 154(b) by 487 days.

(21) Appl. No.: 10/158,858

(22) Filed: Jun. 3, 2002

(65) Prior Publication Data

US 2003/0228701 A1 Dec. 11, 2003

(51) Int. Cl.
*G01N 21/64* (2006.01)
(52) U.S. Cl. ............ 436/124; 436/125; 436/126; 436/164; 436/166; 436/172
(58) Field of Classification Search ............. 436/164, 436/166, 172, 124–126, 141; 252/408.1
See application file for complete search history.

(56) References Cited

U.S. PATENT DOCUMENTS 5,766,952 A 6/1998 Mann et al.

OTHER PUBLICATIONS

Hissler, M. et al, Platinum Diimine Bis(acetylide) Complexes: Synthesis, Characterization, and Luminescence Properties, Inorg. Chem. (2000) vol. 39, pp. 447-457.*
McGarrah, J. et al, Toward a Molecular Photochemical Device: A triad for Photoinduced Charge Separation Based on a Platinum Diimine Bis(acetylide) Chromophore, (2001) Inorg. Chem. vol. 30, pp. 4510-4511.*
Bariain, C., et al., *Detection of volatile organic compound vapors by using a vapochromic material on a tapered optical fiber*, Applied Physics Letters, vol. 77, No. 15, 2000, pp. 2274-2276.
Hodges, K., et al., *Oxidative Addition of Halogens and Pseudohalogens to Dihalo(1, 10-phenanthroline)platinum (II)*, Inorganic Chemistry, vol. 14, No. 3, 1975, pp. 525-528.
Ciana, L., et al., *Synthesis of 1.4-Bis(4-pyridyl)butadiyne*, J. Heterocyclic Chem., vol. 21, No. 607, 1984, pp. 607-608.
Chan, S., et al., *Organic Light-Emitting Materials Based on Bis(arylacetylide)platinum(II) Complexes Bearing Substituted Bipyridine and Phenanthroline Ligands: Photo- and Electroluminescence from $^3$MLCT Excited States*, Chem. Eur. J 2001, vol. 7, No. 19, 2001, pp. 4180-4190.
Altshuller, A., et al., *Application of Diffusion Cells to the Production of Known Concentrations of Gaseous Hydrocarbons*, Analytical Chemistry, vol. 32, No. 7, 1960, pp. 802-810.

* cited by examiner

Primary Examiner—Jeffrey R. Snay
(74) Attorney, Agent, or Firm—Buchanan Ingersoll PC

(57) ABSTRACT

A luminescent sensory material for the detection of the presence of organo-halogen compounds is described. This material is based on a platinum chromophore functionalized with pyridylacetylide ligands, as shown in Formulae I and II below. These complexes exhibit positive luminescence upon exposure to the vapors of organ-halogen compounds like $CH_2Cl_2$ or $CHCl_3$ with high selectivity over non-chlorinated common organic vapors. Direct relationships between vapor concentration and luminescence intensity are established using thin films prepared from these complexes.

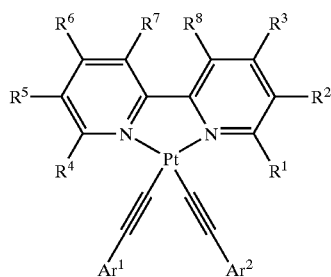

Formula I

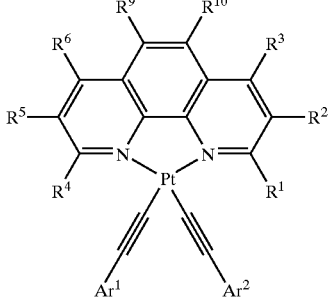

Formula II

14 Claims, 12 Drawing Sheets

LUMINESCENT SENSORY MATERIAL FOR ORGANIC-HALOGEN COMPOUNDS, AND METHODS AND APPARATUS UTILIZING SUCH

FIELD OF THE INVENTION

This invention relates to platinum complexes that can be incorporated into sensor devices for detecting organic-halogen compounds.

BACKGROUND OF THE INVENTION

Organic-halogen compounds, including dichloromethane ($CH_2Cl_2$) and chloroform ($CHCl_3$), are widely used solvents in laboratories, industry and hospitals. However, many of such halogenated compounds are suspected carcinogens and are irritants to the eyes, skin and respiratory system. For example, inhaling the vapors of dichloromethane and chloroform can damage the health of operators due to the extremely high volatility and relatively low olfactory-sensitivity of these two solvents. Also, other organic-halogen compounds such as polychlorinated alkanes and biphenyls have become a significant environmental problem because extremely minute levels are believed to present a health risk. Therefore, there is an increasing need to monitor and screen the presence of organic-halogen compounds in the environment. In particular, sensory materials for dichloromethane, chloroform and other volatile organic compounds (VOCs) with high sensitivity and selectivity are in demand for in vivo environmental monitoring and evaluation.

Luminescent probes provide a convenient method for sensor device design and application. The most common photoluminescence sensor utilizes intensity responses to analytes under conditions of constant irradiation. Ideally, the photoluminescence intensity change is selective, reversible, and sensitive to the analyte of interest. Regardless of the origin, intensity-based sensing has the advantage of being straightforward, inexpensive, and easy to implement. Noble metal complexes have been extensively studied as luminescent sensory materials for pH, cations, anions and so on. Recent progress has also shown that some of these complexes may exhibit vapochromic properties and give luminescent responses in the presence of VOCs and gases. These luminescent probes can be divided into three main types in view of the nature of the vapor-complex interaction mechanism: (a) discrete metallocyclophanes possessing large cavities that can accommodate VOC molecules; (b) oxygen-quenching phosphorescent lumophores tailored into mesoporous materials such as zeolite, rubber and sol-gel; (c) molecular solids that change their crystal lattice or chemical structures upon interaction with vapors.

The electronic structures of square-planar platinum(II) complexes are often sensitive to solid-state effects and the polymorphism of diimine Pt(II) complexes is well known. Recently, the development of luminescent Pt(II) complexes has revealed low-energy excited states. Coordinately unsaturated platinum(II) lumophores and their applications as molecular sensors have also generated immense interest. Many investigations have shown that the color and emissive properties of crystalline Pt(II) diimine salts are highly dependent upon the chosen anion and solvent(s) for the precipitation/recrystallization and differences in the extent of π—π and/or Pt—Pt interactions are usually presumed to be the reason of these phenomena. However, practicable sensory devices for VOCs are still sparse, largely due to ineffective coupling of vapor inhalation (trigger) to emission change (response). Technologically, a "switch-on" sensor is more desirable than a "switch-off" one; that is, there is higher practical value for a solid sensory material that can provide a positive luminescent response for the appearance of vapors and gases.

U.S. Pat. No. 5,766,952 by K. R. Mann et al describes a vapochromic double-complex salt of platinum(II) which changes its color, absorption or emission spectra upon exposure to VOCs, and can therefore be used in sensor devices for environmental evaluation. These Pt(II) complexes are chemically represented by the formulae [Pt(CN—$C_6H_4$-alkyl group)$_4$][Pt(CN)$_4$] and [Pt(diimine)(CN—$C_6H_4$-alkyl group)$_2$][Pt(CN)$_4$]. The deviations of Pt—Pt contacts induced by vapor inhalation are believed to account for the changes in the electronic spectra. However, such complexes are "switch-off" sensors showing negative luminescent response in the presence of $CH_2Cl_2$.

Very recently, a report on detection of volatile organic compound vapors by using a sol-gel material doped with a vapochromic complex of formula [Au(PPh$_2$C(CSSAuC$_6$H$_5$)PPh$_2$Me][ClO$_4$] appeared on *Appl. Phys. Lett.* 2000, 77, 2274. However, the sensing mechanism relies on vapor-induced changes in the refractive index of the film, which may give rise to false signals and therefore may not be specific.

OBJECTS OF THE INVENTION

Therefore, it is an object of this invention to resolve at least one or more of the problems as set forth in the prior art. As a minimum, it is an object of this invention to provide the public with a useful choice.

SUMMARY OF THE INVENTION

Accordingly, this invention provides a platinum complex of the formulae I or II

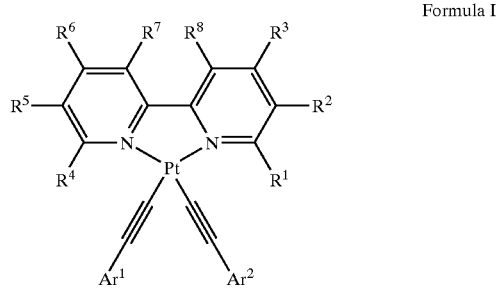

Formula I

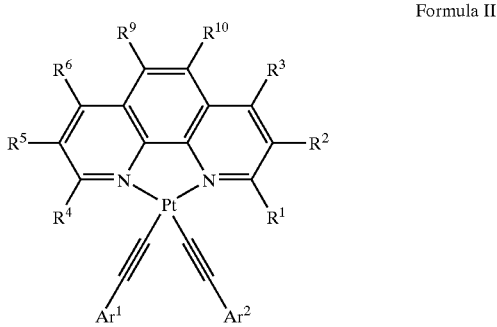

Formula II wherein $R^1$ to $R^{10}$ are each independently hydrogen, alkyl, aryl, alkoxy, halogen, amino or carboxy;

Ar¹ and Ar² are each independently aryl or pyridyl.

It is another aspect of this invention to provide a method of detecting the presence of organic-halogen compounds in a sample by exposing the sample to the above platinum complex of the formulae I or II. If the platinum complex changes color or causes luminescence after being irradiated by a beam of light, such phenomena indicates the presence of said organic-halogen compounds.

It is yet another aspect of this invention to provide a method for preparing the above platinum complex of the formulae I or II. The above platinum complex of the formulae I or II may be synthesized by reacting a platinum complex of the formulae III or IV

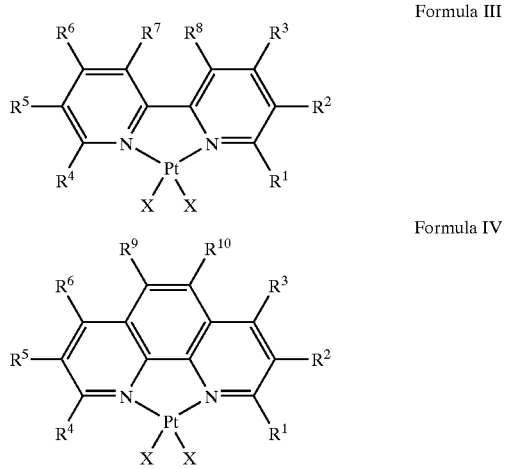

Formula III

Formula IV with at least one of the compounds of the formula V or VI

Formula V

Formula VI in the presence of a base, wherein $R^1$ to $R^{10}$ are each independently hydrogen, alkyl, aryl, alkoxy, halogen, amino or carboxy;

Ar¹ and Ar² are each independently aryl, substituted aryl, pyridyl, substituted pyridyl;

X is selected from the group consisting of Cl, Br, I, —OSO₂—CF₃, —OOC—CF₃.

The alternative embodiments of this invention may be apparent to one skilled in the art, and will be described in the following section.

BRIEF DESCRIPTION OF THE DRAWINGS

Preferred embodiments of the present invention will now be explained by way of example and with reference to the accompany drawings in which.

DETAILED DESCRIPTION OF THE PREFERRED EMBODIMENT

Figure 1:
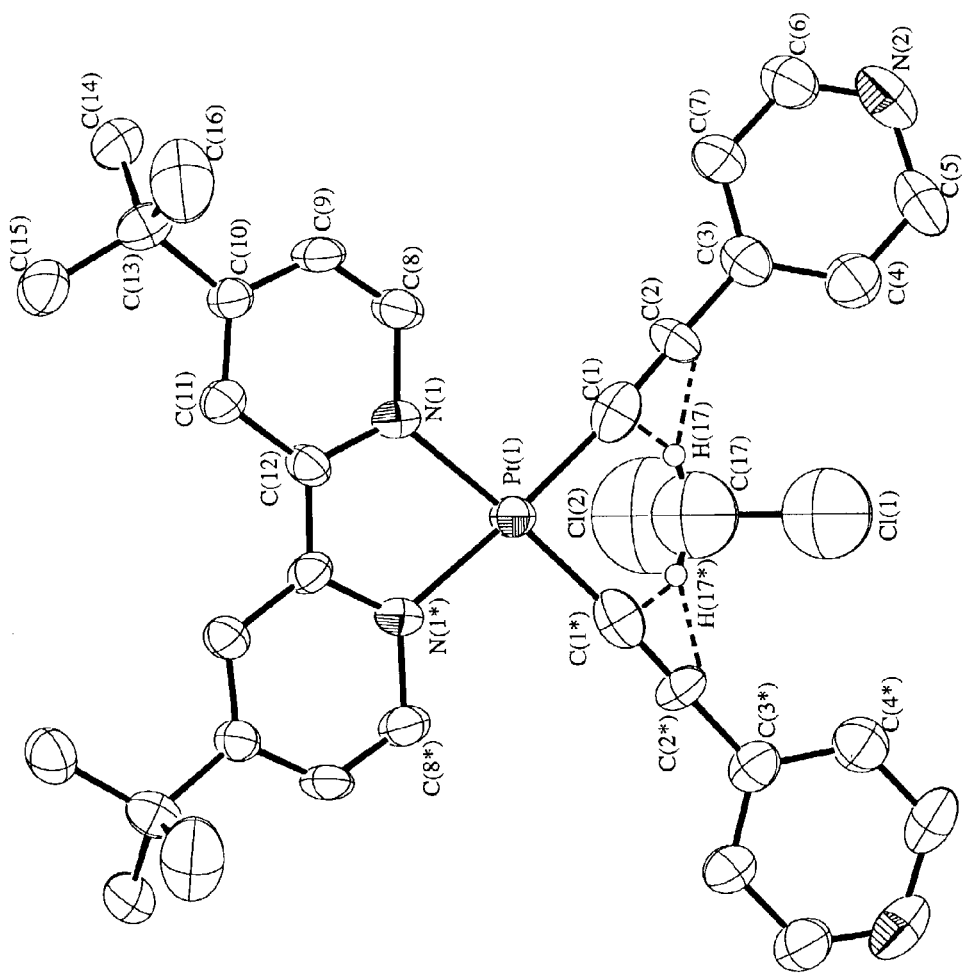
FIG. 1 shows the ORTEP plot of complex 1 CH₂Cl₂ molecule (40% probability ellipsoid). Starred atoms have coordinates at x, ½−y, z.

This invention is now described by ways of example with reference to the figures in the following paragraphs.

In the definitions of the complexes below, collective terms were used which generally represent the following groups:

halogen: fluorine, chlorine, bromine and iodine;

$C_1$–$C_{10}$ alkyl: straight-chain or branched alkyl groups having 1 to 10 carbon atoms, such as methyl, ethyl, propyl, 1-methylethyl, butyl, 1-methylpropyl, 2-methylpropyl, 1,1-dimethylethyl, pentyl, 2-methylbutyl;

$C_1$–$C_{10}$ haloalkyl: straight-chain or branched alkyl groups having 1 to 10 carbon atoms, it being possible for some or all of the hydrogen atoms in these groups to be replaced by halogen atoms as mentioned above, for example $C_1$–$C_{10}$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$–$C_{10}$ alkoxy: straight-chain or branched alkyl groups having 1 to 10 carbon atoms as mentioned above, which are attached to the skeleton via an oxygen atom (——O——), for example $C_1$–$C_{10}$ alkoxy such as methyloxy, ethyloxy, propyloxy, 1-methylethyloxy, butyloxy, 1-methylpropyloxy, 2-methylpropyloxy, 1,1-dimethylethyloxy;

$C_1$–$C_{10}$ halo-alkoxy: straight-chain alkyl groups having 1 to 10 carbon atoms, it being possible for some or all of the hydrogen atoms in these groups to be replaced by halogen atoms as mentioned above, these groups being attached to the skeleton via an oxygen atom, for example chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy.

The term "partially or fully halogenated" is meant to express that in the groups characterized in this manner the hydrogen atoms may be partially or fully replaced by identical or different halogen atoms as mentioned above.

The objects of the present invention may be fulfilled by a novel chemosensory material for the detection of organic halogen compounds. This material is based on the diimine platinum complex functionalized with pyridylacetylide ligands. The chemical structure of this complex is shown in Formulae I and II below:

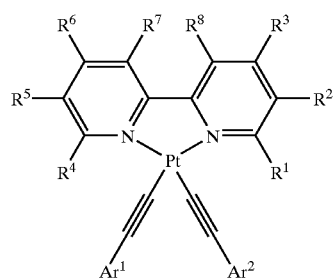

Formula I

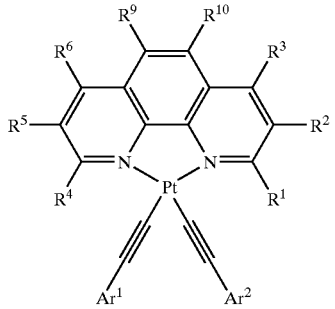

Formula II wherein
R$^1$ to R$^{10}$ are each independently hydrogen, alkyl, aryl, alkoxy, halogen, amino or carboxy, where the alkyl and aryl radical may carry one or, independently of one another, two or three of the following substituents: halogen, cyano, amino, sufonyl, nitro, C$_1$–C$_4$ alkyl, C$_1$–C$_2$ haloalkyl, C$_1$–C$_4$ alkoxy, or C$_1$–C$_2$ haloalkoxy;
Ar$^1$ and Ar$^2$ are each independently aryl and pyridyl, where the aryl and pyridyl radical may carry one or, independently of one another, two or three of the following substituents: halogen, cyano, amino, sufonyl, nitro, C$_1$–C$_4$ alkyl, C$_1$–C$_2$ haloalkyl, C$_1$–C$_4$ alkoxy, or C$_1$–C$_2$ haloalkoxy.

This novel material provides 'switch-on' luminescence upon exposure to organic-halogen compounds, like the vapors of CH$_2$Cl$_2$ or CHCl$_3$, with high selectivity. The compounds may be prefered to be used as a crystalline powder. If the compounds are used in solution, the detection speed may be lower due to the time required to exchange the solvated solvent molecule by the organic-halogen compounds. The vapor inhalation and corresponding emission changes may be reversible, and the monitored emission wavelength (450–650 nm) for complex 1 that will be described below falls into the visible range. Quantitative studies show that thin films of this sensory material display substantial luminescence enhancement in the presence of organic-halogen compounds like CH$_2$Cl$_2$ and CHCl$_3$ vapors but not for other VOCs, for example, acetonitrile, acetone, toluene, methanol and ethanol. No obvious difference is observed when the carrier gas is oxygen or air. Quantitative studies with thin films of this material show that good linearity is obtained in complex 1 between vapor concentration and luminescence intensity for CH$_2$Cl$_2$ and CHCl$_3$ respectively in the concentration range of 0–3×10$^4$ ppm. A film deposited with complex 1 is more sensitive for CH$_2$Cl$_2$ (detected limit ~25 ppm) compared to CHCl$_3$ (detected limit ~450 ppm).

The present invention is generally directed to syntheses, and structural and spectroscopic properties of a novel luminescent sensory material and its applications in detecting the vapors of dichloromethane and chloroform. Special design features of this sensory material include:

The diimine Pt(II) luminophore was chosen as the signaling component due to the highly sensitive nature of its excited state in the solid state.
  The acetylide ligand was chosen to facilitate long range electronic communication as a result of its highly conjugated electronic structure.
  The metal-acetylide moiety was chosen due to its eletron-rich property which favors C—H..π(C≡C) interactions between acetylide triple bonds and acidic protons, such as those in dichloromethane and chloroform.
  The aryl pyridyl group in the acetylide ligand was chosen as a quenching component which 'turns off' the luminescence in the resting state.

Synthesis of the Complexes

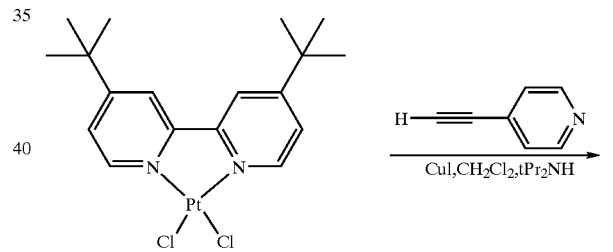

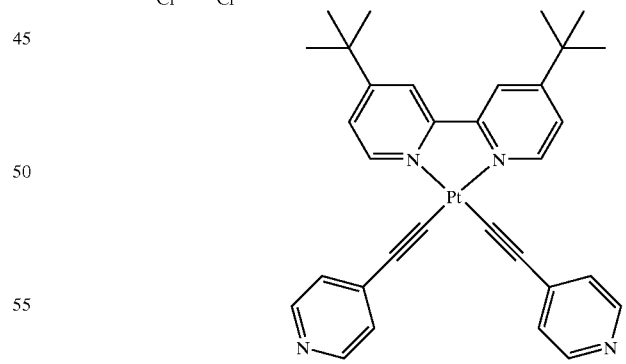

Complex 1

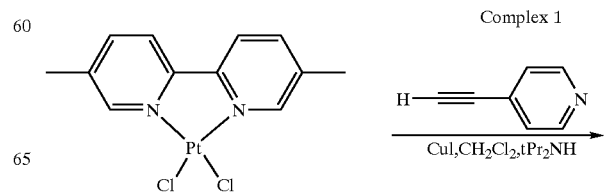

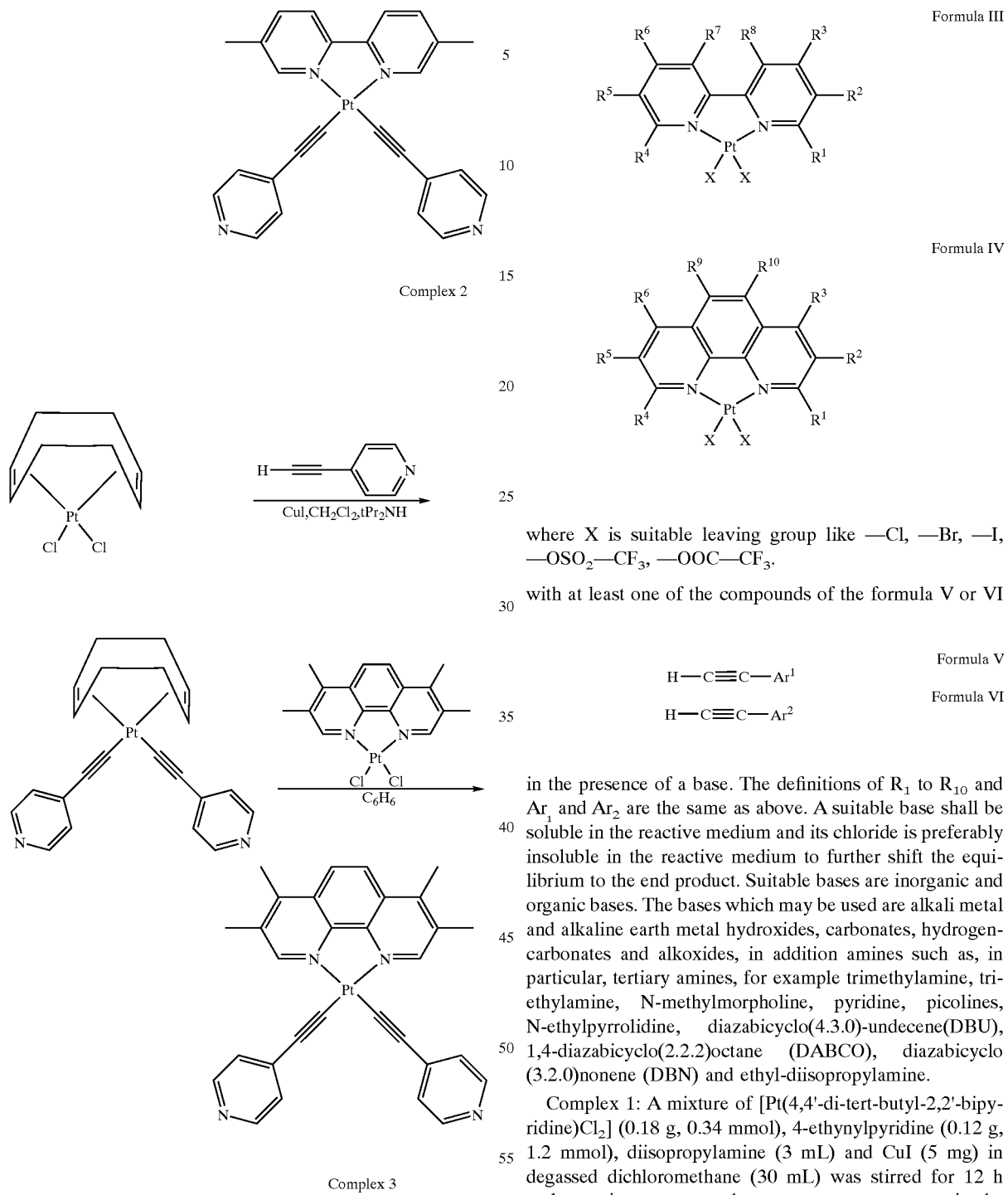

Complex 2

Complex 3

The starting materials [Pt(diimine)Cl$_2$] (K. D. Hodges et al, *Inorg. Chem.* 1975, 14, 525) and 4-ethynylpyridine (L. D. Ciana et al, *J. Heterocyclic Chem.* 1984, 21, 607) were prepared according to literature methods. The other chemicals were obtained from commercial sources.

Generally, the platinum complexes of this invention is synthesized by reacting a platinum complex of the formula III or IV where X is suitable leaving group like —Cl, —Br, —I, —OSO$_2$—CF$_3$, —OOC—CF$_3$.

with at least one of the compounds of the formula V or VI $$H-C\equiv C-Ar^1 \quad \text{Formula V}$$
$$H-C\equiv C-Ar^2 \quad \text{Formula VI}$$

in the presence of a base. The definitions of R$_1$ to R$_{10}$ and Ar$_1$ and Ar$_2$ are the same as above. A suitable base shall be soluble in the reactive medium and its chloride is preferably insoluble in the reactive medium to further shift the equilibrium to the end product. Suitable bases are inorganic and organic bases. The bases which may be used are alkali metal and alkaline earth metal hydroxides, carbonates, hydrogencarbonates and alkoxides, in addition amines such as, in particular, tertiary amines, for example trimethylamine, triethylamine, N-methylmorpholine, pyridine, picolines, N-ethylpyrrolidine, diazabicyclo(4.3.0)-undecene(DBU), 1,4-diazabicyclo(2.2.2)octane (DABCO), diazabicyclo (3.2.0)nonene (DBN) and ethyl-diisopropylamine.

Figure 2:
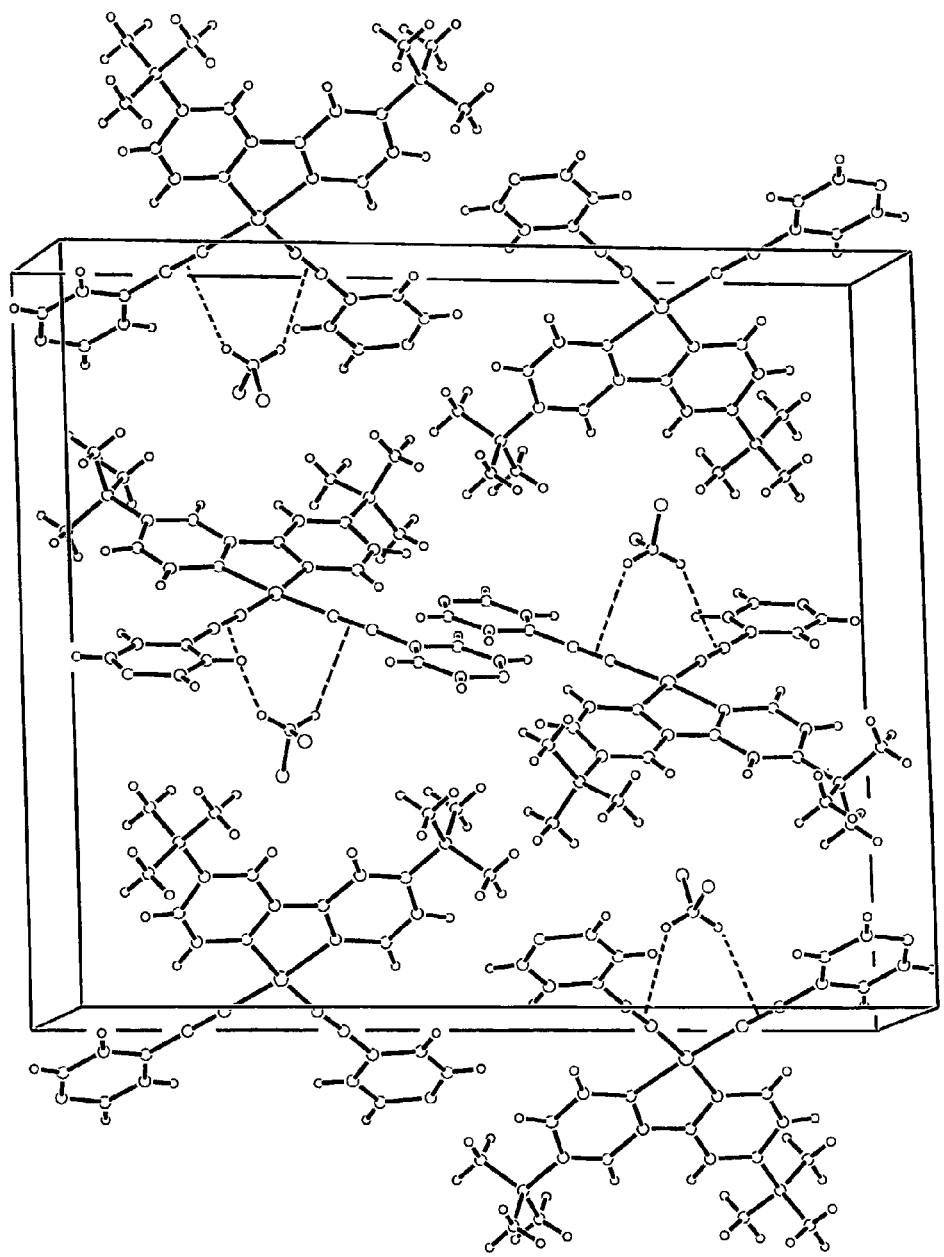
FIG. 2 shows the molecular packing diagram of complex 1 CH₂Cl₂ clathrate.
Figure 3:
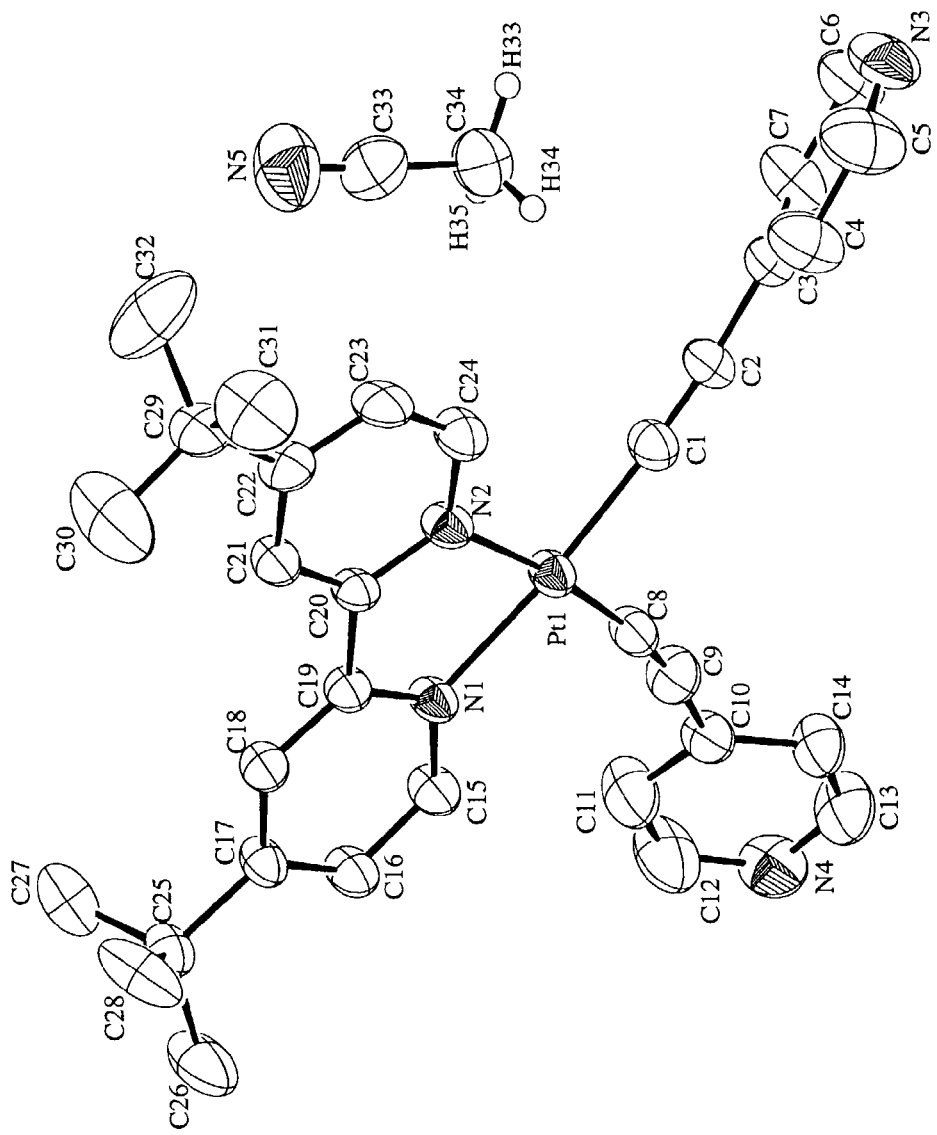
FIG. 3 shows the ORTEP plot of complex 1 CH₃CN molecule (40% probability ellipsoid).

Complex 1: A mixture of [Pt(4,4'-di-tert-butyl-2,2'-bipyridine)Cl$_2$] (0.18 g, 0.34 mmol), 4-ethynylpyridine (0.12 g, 1.2 mmol), diisopropylamine (3 mL) and CuI (5 mg) in degassed dichloromethane (30 mL) was stirred for 12 h under a nitrogen atmosphere at room temperature in the absence of light. The resulted yellow solution was evaporated to dryness. The crude product was purified by flash chromatography (neutral Al$_2$O$_3$, CH$_2$Cl$_2$ as eluent) and recrystallized from dichloromethane/diethyl ether to give greenish-yellow needles (0.2 g, 88% yield) or from acetonitrile to give yellow prisms. IR (Nujol): ν=2116, 2128 (m, C≡C) cm$^{-1}$; FAB MS: 668 (M$^+$+H); elemental analysis (%): calcd for C$_{32}$H$_{32}$N$_4$PtCH$_2$Cl$_2$: C 52.66, H 4.55, N 7.44; found: C 52.83, H 4.54, N 7.05; $^1$H NMR (300 MHz, CDCl$_3$, 22° C., TMS): δ=9.56 (d, 2H, J=6.0 Hz), 8.46 (d, 4H, J=4.6 Hz), 7.99 (s, 2H), 7.63 (d, 2H, J=6.0 Hz), 7.35 (d, 4H, J=4.6 Hz), 1.45 (s, 18H). $^{13}C\{^1H\}$ NMR (400 MHz, $CD_2Cl_2$, 22° C., TMS): δ=166.1, 157.9, 152.4, 151.0, 137.4, 127.9, 126.6, 121.1, 101.3, 97.0, 37.5, 31.6. Depending on the recrystallization solvent, two types of solvated crystals, namely 1 $CH_2Cl_2$ and 1 $CH_3CN$ were obtained and resolved by X-ray crystallography; these revealed different crystal lattices related to deviations in C—H..π (C≡C) interactions. In 1 $CH_2Cl_2$, a structure with $C_{2v}$ symmetry was found (FIG. 1). The dichloromethane molecule is located below the plane defined by the diimine-Pt moiety and weakly interacts with both of the acetylenic triple bonds. The average distance between the protons of $CH_2Cl_2$ and acetylenic carbon atoms is 2.7 Å. Hence weak C—H..π (C≡C) interactions between the acetylenic units and the $CH_2Cl_2$ molecules are apparent. The molecular packing diagram of 1 $CH_2Cl_2$ is shown in FIG. 2. We can regard 1 $CH_2Cl_2$ as a 1/1 (host/guest) clathrate crystal. The 1 $CH_3CN$ molecule (FIG. 3) is not $C_{2v}$ symmetric, and the distances between acetylenic carbon atoms and protons of the $CH_3CN$ molecules are ~3 Å which is plausible for a defined assignment of C—H..π (C≡C) interaction.

Complex 2: A mixture of [Pt(3,3'-dimethyl-2,2'-bipyridine)$Cl_2$] (0.15 g, 0.30 mmol), 4-ethynylpyridine (0.12 g, 1.2 mmol), diisopropylamine (3 mL) and CuI (5 mg) in degassed dichloromethane (30 mL) was stirred for 12 h under a nitrogen atmosphere at room temperature in the absence of light. The resulted suspension was filtered and the orange powder was collected after washing with $CH_2Cl_2$ and diethyl ether. FAB MS: 583 ($M^+$+H); $^1H$ NMR (300 MHz, DMSO-$d_6$, 22° C., TMS): δ=9.24 (d, 2H, J=6.5 Hz), 8.58 (s, 2H), 8.40 (d, 4H, J=4.0 Hz), 7.71 (d, 2H, J=6.4 Hz), 7.28 (d, 4H, J=4.3 Hz), 2.52 (s, 6H).

Complex 3: A mixture of [Pt(COD)$Cl_2$] (0.50 g, 1.3 mmol), 4-ethynylpyridine (0.31 g, 3.0 mmol), diisopropylamine (10 mL) and CuI (20 mg) in degassed dichloromethane (100 mL) was stirred for 12 h under a nitrogen atmosphere at room temperature in the absence of light. The resulted suspension was filtered and the off-white powder was collected after washing with $CH_2Cl_2$ and diethyl ether. $^1H$ NMR (300 MHz, $CDCl_3$, 22° C., TMS): δ=8.44 (d, 4H, J=4.6 Hz), 7.22 (d, 4H, J=4.6 Hz), 5.73 (s, 4H, with 195Pt satellites, $J_{Pt-H}$=45.1 Hz), 2.61 (s, 8H). A mixture of the obtained powder (0.10 g, 0.2 mmol), [Pt(3,4,7,8-tetramethyl-1,10-phenanthroline)$Cl_2$] (0.10 g, 0.2 mmol) in degassed benzene (50 mL) was refluxed for 24 h under a nitrogen atmosphere. The resulted suspension was filtered and the orange powder was collected after washing with $CH_2Cl_2$ and diethyl ether. FAB MS: 635 ($M^+$+H).

Spectroscopic Properties of the Complexes

Figure 4:
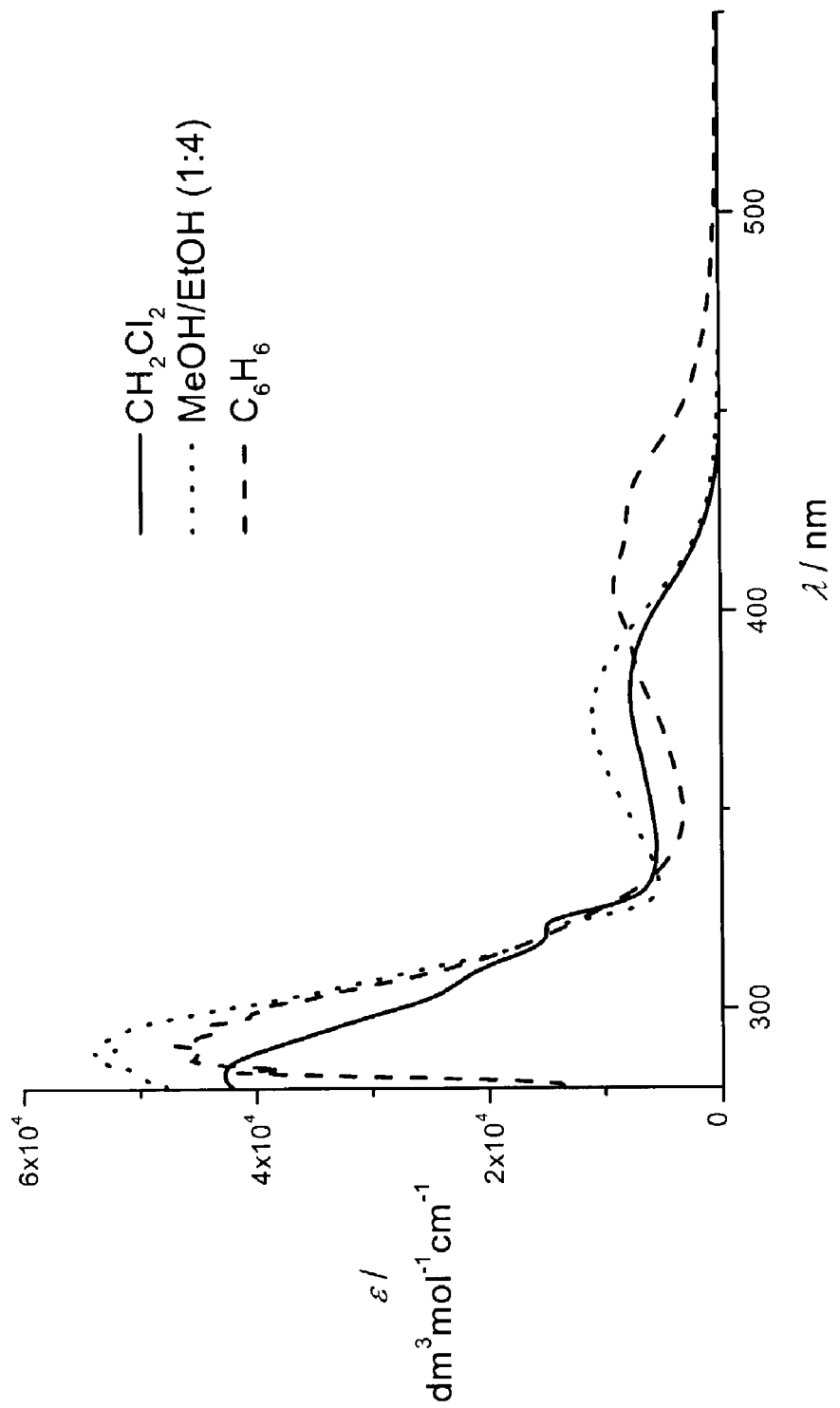
FIG. 4 shows the UV-vis absorption spectra of complex 1 in different solvents at 298 K.
Figure 5:
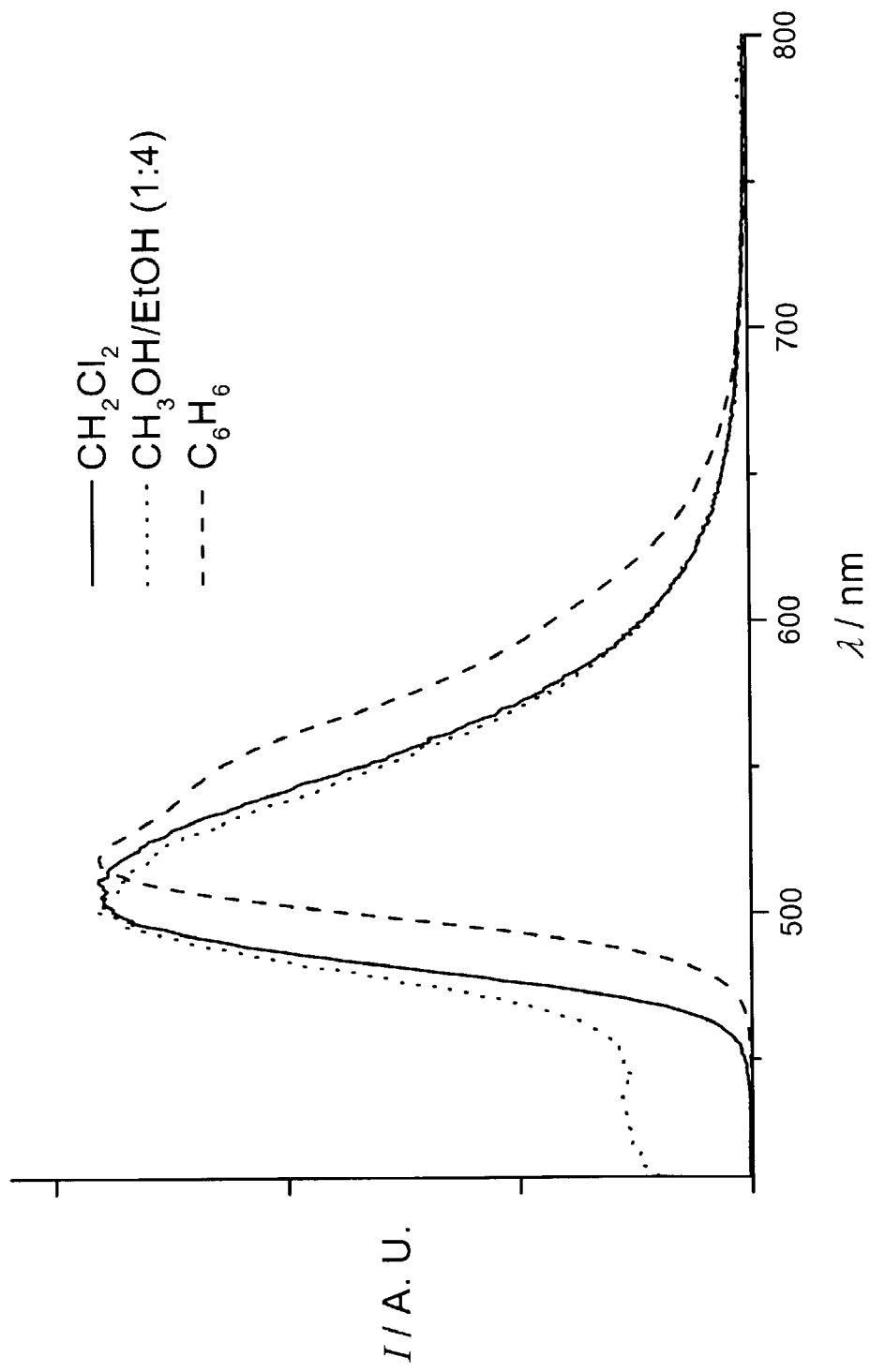
FIG. 5 shows the normalized emission spectra of complex 1 in different solvents at 298 K (I=intensity, $\lambda_{ex}$=350 nm).
Figure 6:
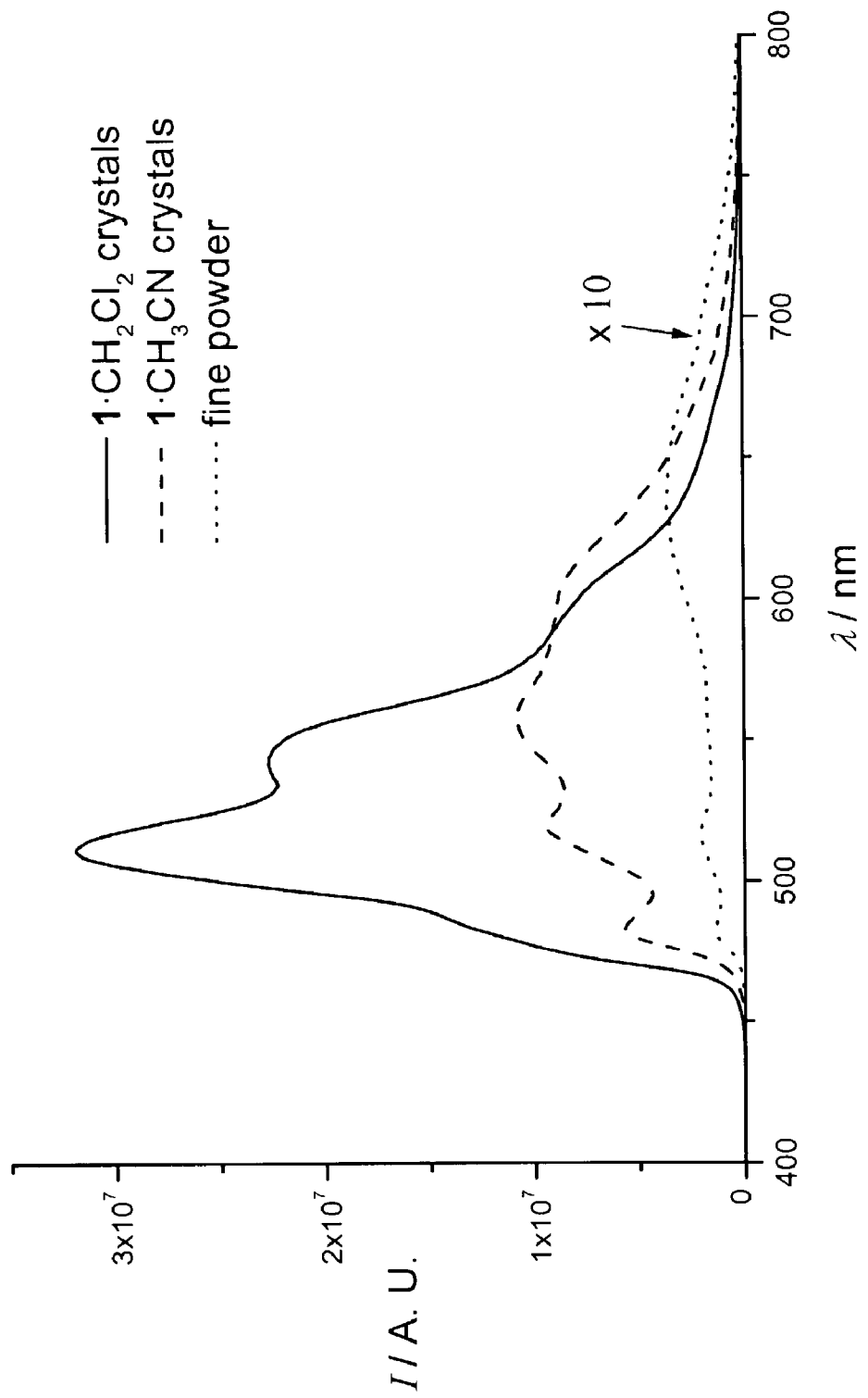
FIG. 6 shows the uncorrected solid emission spectra of complex 1 with different crystallinity (I=intensity, $\lambda_{ex}$=350 nm).

In $CH_2Cl_2$, complex 1 displays an intense UV absorption band around 290 nm and a modest absorption band around 380 nm which tails beyond 450 nm at room temperature (FIG. 4). Complex 1 is highly luminescent in fluid solution (FIG. 5). The emission maximum is 501, 510 and 519 nm in methanol/ethanol (1:4), dichloromethane and toluene (quantum yield ~0.6), respectively, and a metal-ligand charge transfer (MLCT) excited state is proposed to be responsible. Moreover, the solid-state emission for this complex is dependent on the sample crystallinity. As shown in FIG. 6, crystals with solvated $CH_2Cl_2$ molecules feature the most intense emission at $\lambda_{max}$ 517 nm with vibronic progressions of around 1300 $cm^{-1}$. This emission is believed to be MLCT Pt(5d)→π*(diimine). Crystals with solvated $CH_3CN$ molecules exhibit modestly intense emission at $\lambda_{max}$ 560 nm with similar vibronic progressions in the range of 480–600 nm. This transition may be modified by different $R_1$ to $R_{10}$ and substituents in $Ar_1$ and/or $Ar_2$ in the acetylide ligands, and will in turn alter the wavelength of the transmission. In particular, modifying substituents in $Ar_1$ and/or $Ar_2$ may have a stronger influence to the MLCT emission. Therefore the color of the emission may be modified by different $R_1$ to $R_{10}$ and substituents in $Ar_1$ and/or $Ar_2$.

$R_7$ and $R_8$ are preferably hydrogen if the platinum complex has the formula I, as other substituents may introduce steric distortion to the diimine ligand. This may distort the overall structure of the platinum complex, and affect the MLCT emission. $R_1$ and $R_4$ are also preferably hydrogen for both formula I and II due to the same reason.

Organic-halogen compounds other than $CH_2Cl_2$ and $CHCl_3$ may also be detected by the platinum complexes of this invention. Suitable modification to complex 1 using different $R_1$ to $R_{10}$ and substituents in $Ar_1$ and/or $Ar_2$ may be required to alter the separation between the two acetylide ligands to accommodate organic-halogen compounds larger than $CH_2Cl_2$ and $CHCl_3$ like bromomethane, triflo-romethane, iodoethane.

The fine powder of complex 1, obtained by grinding crystals using mortar and pestle, is only weakly, almost negligibly, emissive. In attempts to synthesize other diimine Pt(II) pyridylacetylide complexes (such as complexes 2 and 3), we obtained sparsingly soluble dull yellow powders with weak orange emission upon UV stimulation. No vapochromic phenomenon was found with bis-phenylacetylide congeners (S. C. Chan et al, *Chem. Eur. J.* 2001, vol. 7, issue 19, pp. 4180–4190), thus the pyridyl substituent appears to play a critical role in the switching process. When the dull yellow powder from complex 1 was exposed to an atmosphere of dichloromethane or chloroform, the powder changed to a bright yellow-green color immediately and emitted intense green light upon 354 nm UV excitation. Importantly, this color change and emission enhancement was not observed for other organic vapors, including $CH_3CN$. Exposure to reduced pressure for several minutes resulted in the restoration of the original dull yellow appearance. Thus the change in color and/or intensity of luminescence is reversible. This implies that the solid-state lattice of complex 1 selectively allows absorption of the dichloromethane and chloroform vapors and this results in a concomitant change in the emissive excited state.

Film Behavior

Complex 1 (20 mg) was dissolved in $CH_2Cl_2$ (20 mL) in a beaker. A piece of glass slide (2 cm×2 cm), pretreated by HF solution, was placed on the bottom of the complex solution. Diethyl ether vapor was allowed to diffuse slowly into this solution. After 20–30 hours, the glass slide with microcrystalline complex 1 on the surface was removed and used for subsequent measurements. The thickness of the film, as determined with scanning electron microscopy, was around 20–50 μm.

Figure 7:
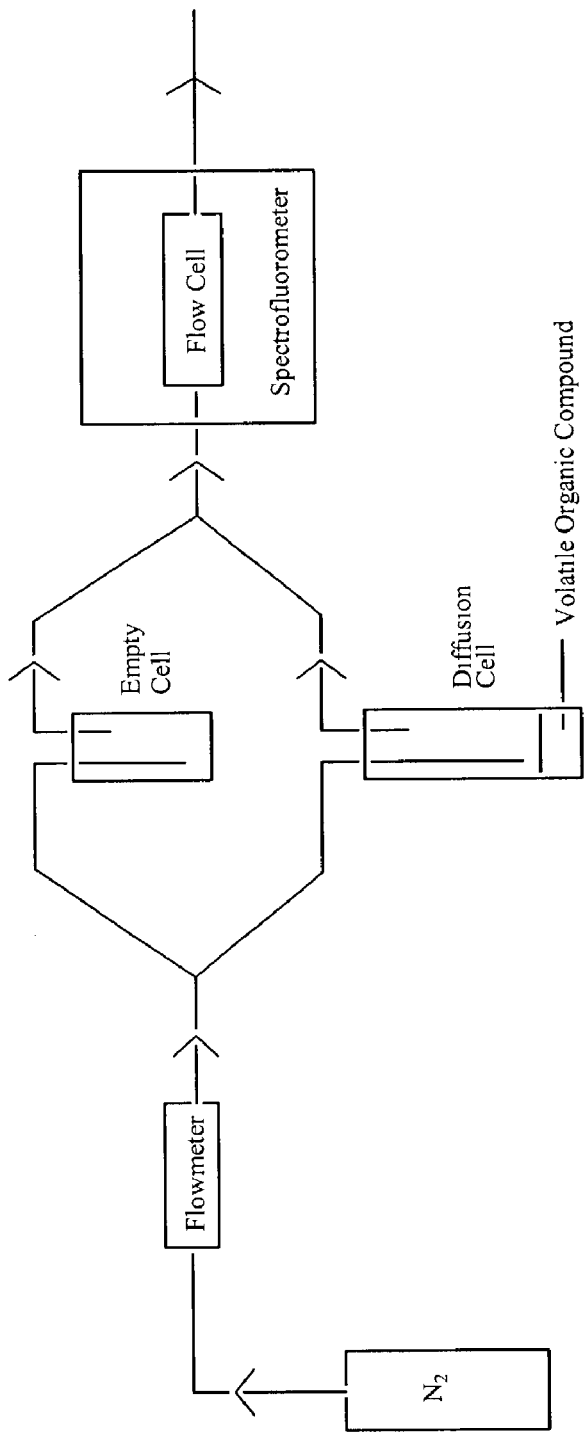
FIG. 7 shows the schematic diagram of the set-up for determining the emission response of the sensing films towards VOCs.
Figure 7:
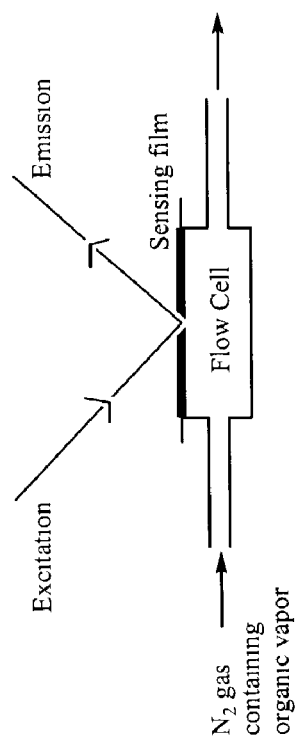

A schematic diagram showing the set-up for determining the emission response of the sensing film towards organic vapors is shown in FIG. 7. Briefly, organic vapors of various concentrations were produced by the diffusion tube method (A. P. Atshuller et al, *Anal. Chem.* 1960, 32, 802). The $N_2$ gas containing the organic vapor was fed into a flow cell in which the sensing film was exposed to the gas stream; the glass slide was facing the excitation light source in the spectrofluorometer. A Perkin-Elmer LS-50B spectrofluorometer was used in all measurements.

Figure 8:
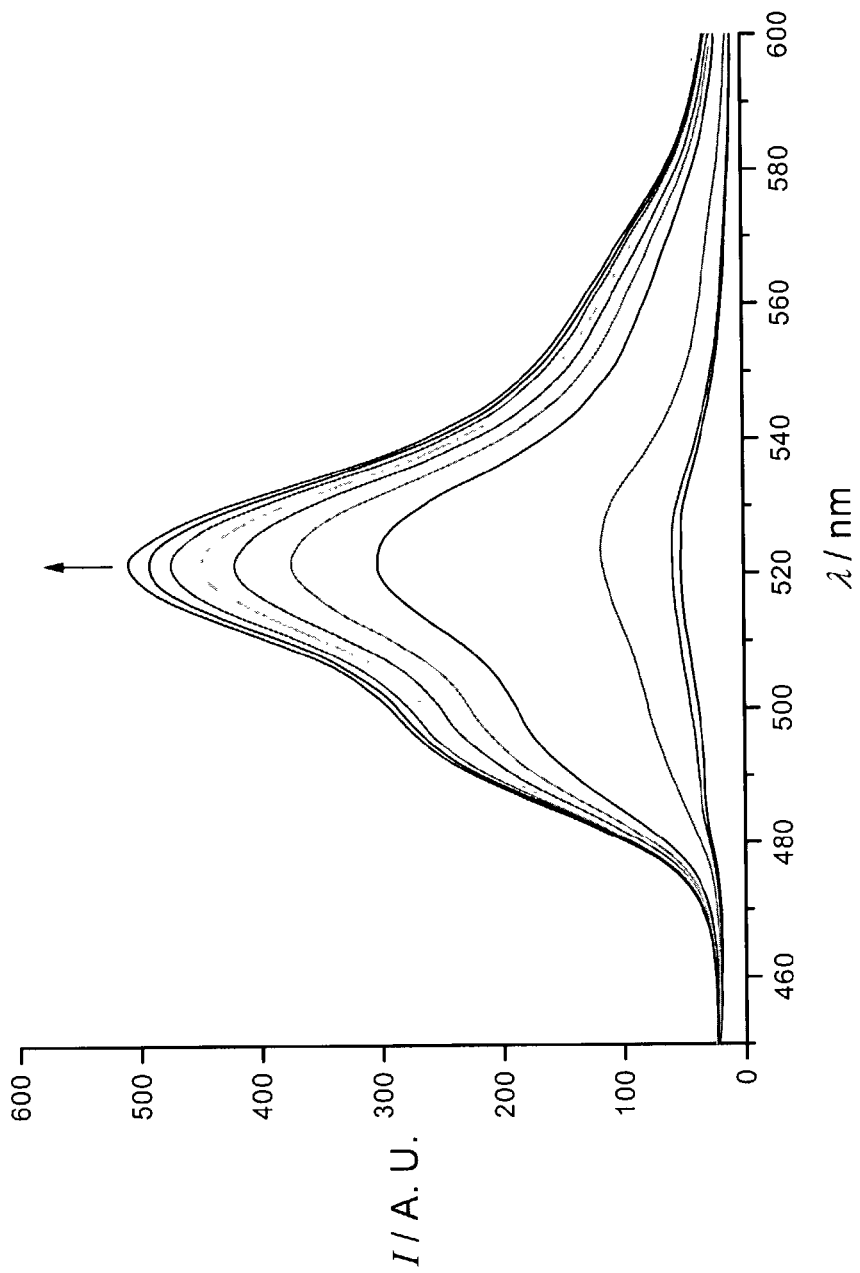
FIG. 8 shows the emission spectral traces for a film prepared with complex 1 in the presence of N₂ saturated with CH₂Cl₂ vapor (I=luminescent intensity, $\lambda_{ex}$=350 nm, N₂ flow rate=12 mL/min, interval=2 min).
Figure 9:
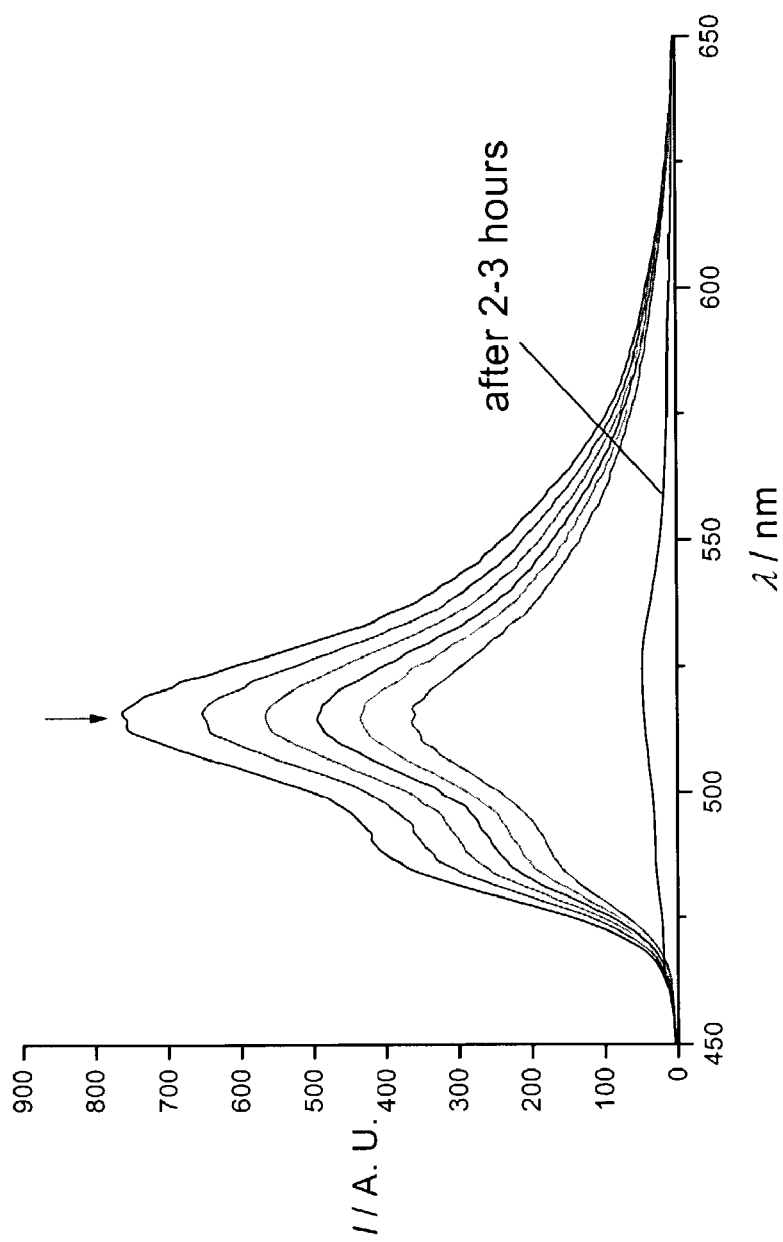
FIG. 9 shows the emission spectral traces for the film in FIG. 8 upon removal of CH₂Cl₂ vapor with N₂ gas ($\lambda_{ex}$=350 nm, carrier flow rate=90 mL/min, interval=2 min).
Figure 10:
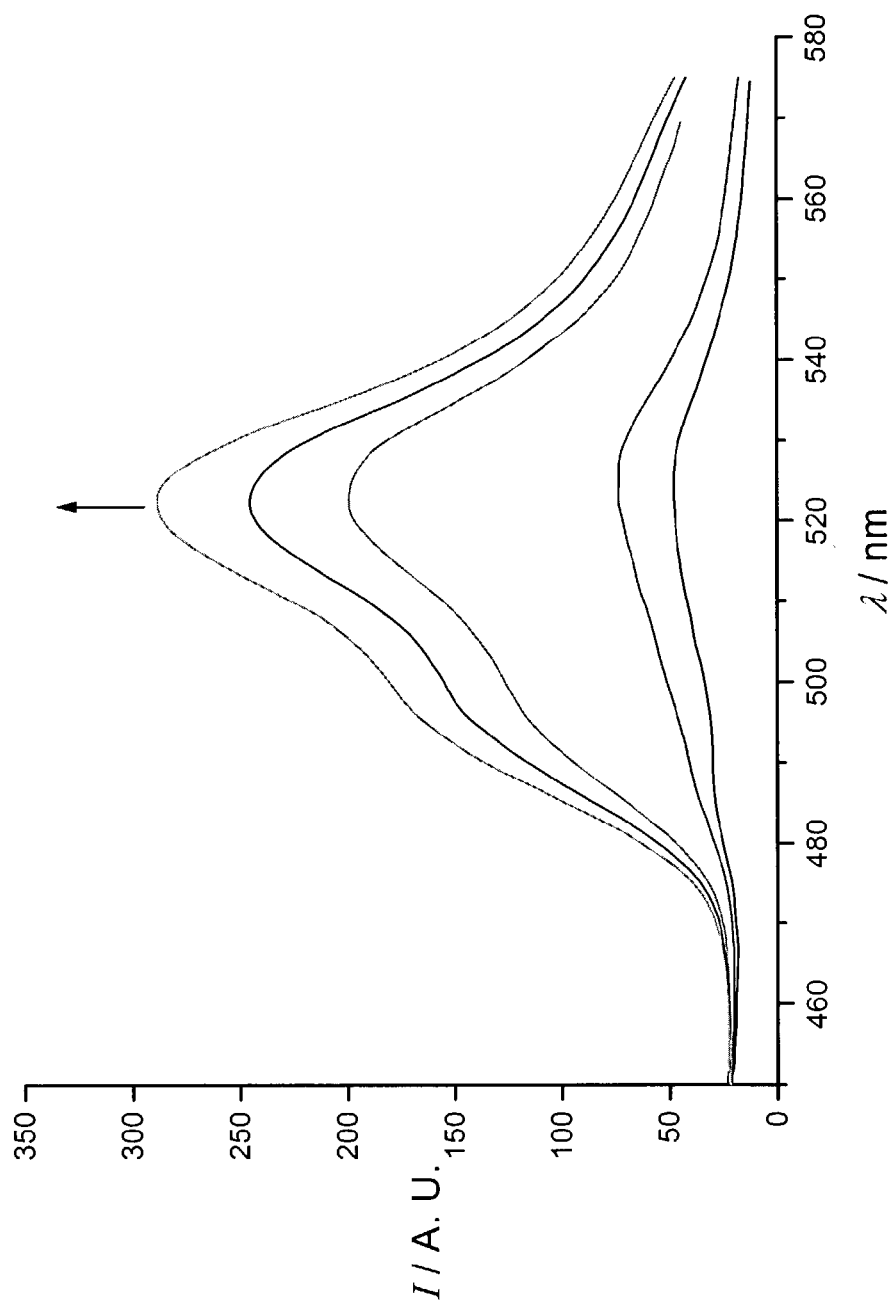
FIG. 10 shows the emission spectral traces for a film prepared with complex 1 in the presence of N₂ saturated with CHCl₃ vapor (I=luminescent intensity, $\lambda_{ex}$=350 nm, N₂ flow rate=12 mL/min, interval=2 min).
Figure 11:
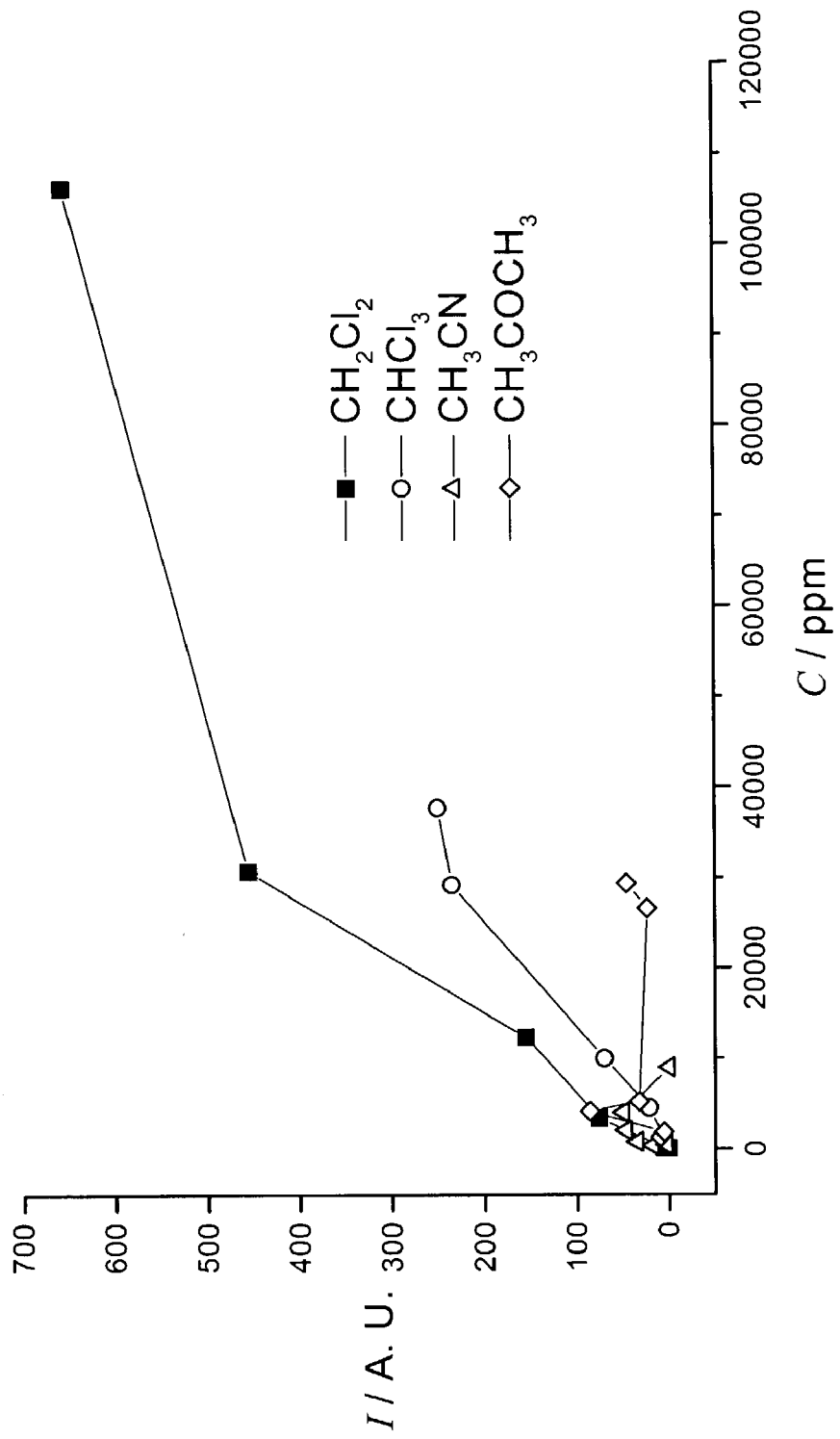
FIG. 11 shows the relative emission intensity (I) versus vapor concentration (C) of different VOCs for a film prepared with complex 1 (monitored at 515 nm, $\lambda_{ex}$=350 nm).
Figure 12:
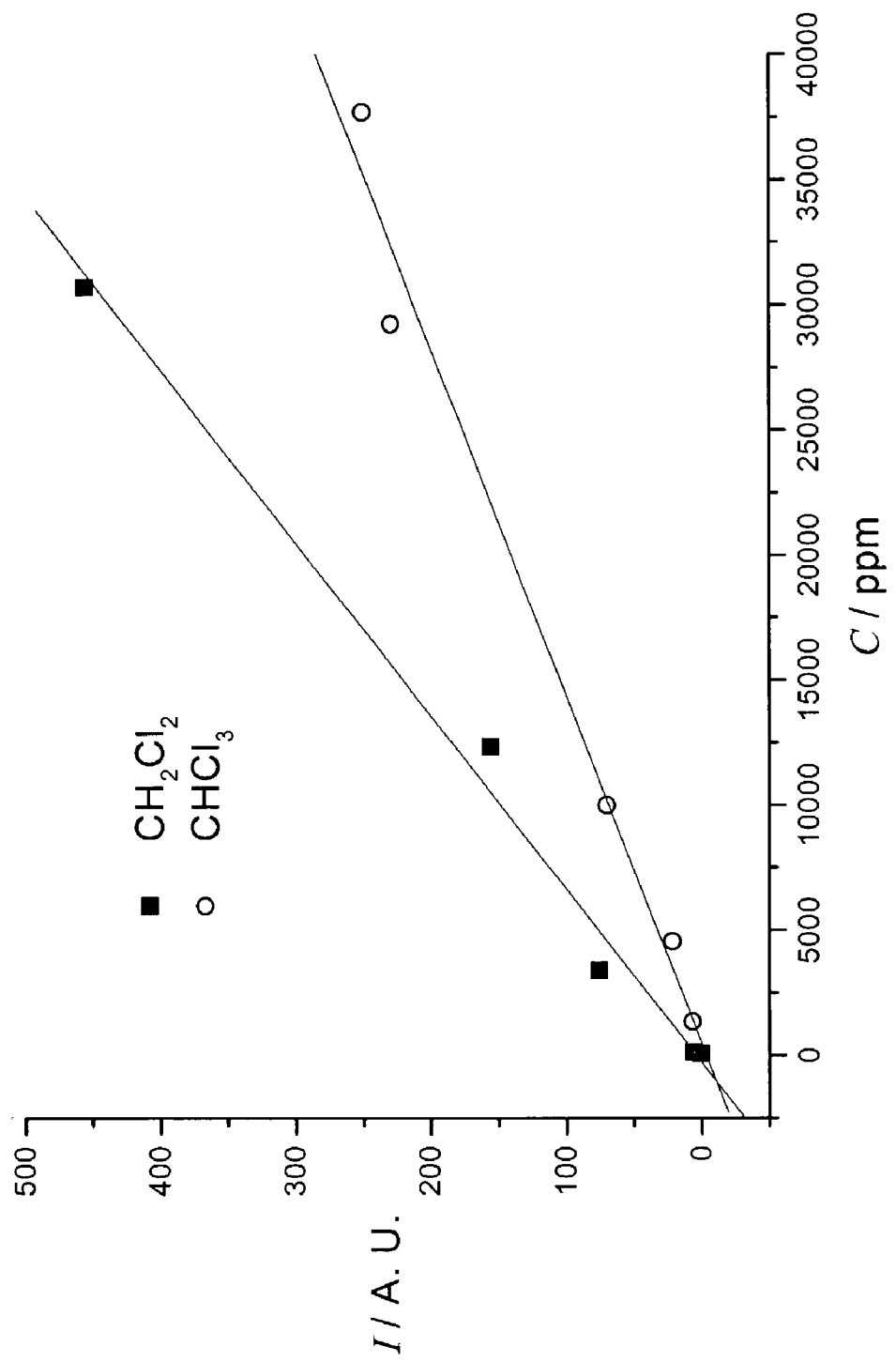
FIG. 12 shows the relative emission intensity (I) versus vapor concentration (C) of CH₂Cl₂ and CHCl₃ for the film in FIG. 11 (monitored at 515 nm, $\lambda_{ex}$=350 nm).

In the absence of VOC vapor, the films gave little residual emission signal. Upon introduction of $N_2$ gas saturated with $CH_2Cl_2$ vapor, a structured emission developed to give a strong 'on' response (FIG. 8), and after 30 min, the emission reached its steady state. However, upon removal of the $CH_2Cl_2$ vapor with nitrogen carrier, the emission intensity significantly decreased (FIG. 9), and returned to the 'off' state after 2–3 hours. This process was also observed for $CHCl_3$ vapor (FIG. 10) but not for other VOCs, for example, acetonitrile, acetone, toluene, methanol or ethanol. A comparison of the emission intensity for a film in the presence of $CH_2Cl_2$, $CHCl_3$, $CH_3CN$ and $CH_3COCH_3$ vapor is shown in FIG. 11. No obvious influence was observed when the $N_2$ gas was replaced by oxygen or air. The emission intensity at 515 nm for various vapor concentrations of $CH_2Cl_2$ and $CHCl_3$ was recorded, and good linearity was obtained in the vapor concentration range $0-3\times10^4$ ppm (FIG. 12). As indicated by the slopes of the fitted lines, the film is more sensitive for $CH_2Cl_2$ than for $CHCl_3$. The response ranges and other relevant data of this film for various volatile organic compounds are list in Table I (the detection limit is the minimum concentration of organic compound that can be detected at three times of the standard deviation above the blank signal):

TABLE I

|  | $CH_2Cl_2$ | $CHCl_3$ | $CH_3COCH_3$ | $CH_3CN$ |
| --- | --- | --- | --- | --- |
| Linear range/ppm | 70–30700 | 1360–37700 | 1863–6300 | 360–2024 |
| Response range/ppm | 70–106088 | 1360–37700 | 1863–29300 | 360–9000 |
| Detection limit/ppm | 25 | 450 | 620 | 125 |

Thus, it was shown that the platinum complexes of this invention can provide a "switch-on" sensor showing positive luminescent response in the presence of organic-halogen compounds. Further, the platinum complexes can be used as direct deposition to film, thus avoiding detecting change in refractive index of the film. Accordingly, the resulting detection method can be more specific.

While the preferred embodiment of the present invention has been described in detail by the examples, it is apparent that modifications and adaptations of the present invention will occur to those skilled in the art. It is to be expressly understood, however, that such modifications and adaptations are within the scope of the present invention, as set forth in the following claims. Furthermore, the embodiments of the present invention shall not be interpreted to be restricted by the examples or figures only.

The invention claimed is:

1. A platinum complex of the formulae I or II

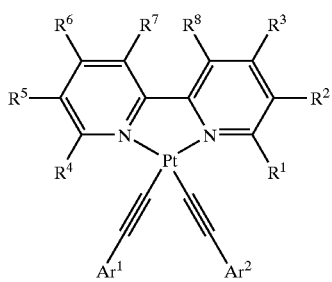

Formula I

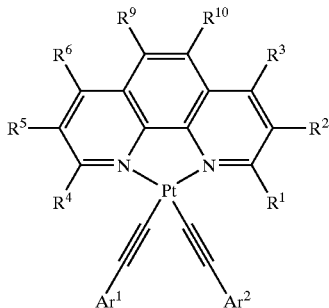

Formula II wherein $R^1$ to $R^{10}$ are each independently hydrogen, alkyl, aryl, alkoxy, halogen, amino or carboxy;

$Ar^1$ and $Ar^2$ are each independently pyridyl.

2. The platinum complex of claim 1 of the formula I, wherein $R^7$ and $R^8$ are hydrogen.

3. The platinum complex of claim 2, wherein $R^1$ and $R^4$ are hydrogen.

4. The platinum complex of claim 3, wherein $R^3$ and $R^6$ are t-butyl.

5. The platinum complex of claim 3, wherein $R^2$ and $R^5$ are methyl.

6. The platinum complex of claim 1, where both $Ar^1$ and $Ar^2$ are 4-pyridyl.

7. The platinum complex of claim 1 of the formula II, wherein $R^1$ and $R^4$ are hydrogen.

8. The platinum complex of claim 7, wherein $R^2$, $R^3$, $R^5$, and $R^6$ are methyl.

9. A method of detecting the presence of organic-halogen compound in a sample including the steps of:

exposing said sample to a platinum complex and of the formulae I or II

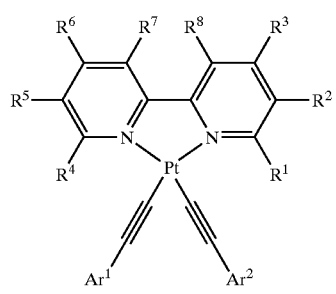

Formula I

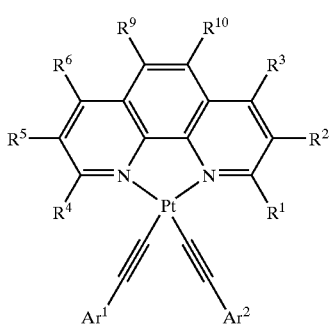

Formula II wherein
R$^1$ to R$^{10}$ to are each independently hydrogen, alkyl, aryl, alkoxy, halogen, amino or carboxy; and
Ar$^1$ and Ar$^2$ are each independently aryl or pyridyl; and
sensing or observing whether
   a) the platinum complex changes color; or
   b) the platinum complex causes luminescence after being irradiated by a beam of light,
   wherein such a color change or luminescence indicate the presence of said organic-halogen compound.

10. The method of claim 9, wherein the organic-halogen compound comprises dichloromethane or trichloromethane.

11. The method of claim 9, wherein vapor of said sample is exposed to the platinum complex.

12. The method of claim 9, wherein the beam of light has a wavelength of 300 to 400 nm.

13. A method for preparing the platinum complex as claimed in claim 1, including the steps of reacting a platinum complex of the formulae III or

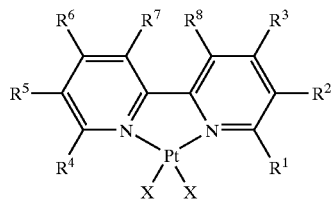

Formula III with at least one of the compounds of the formula V or VI

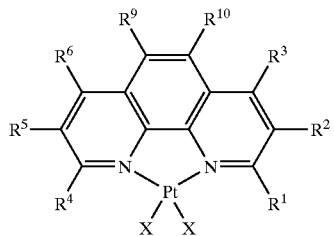

Formula IV

Formula V

Formula VI in the presence of a base, wherein
R$^1$ to R$^{10}$ are each independently hydrogen, alkyl, aryl, alkoxy, halogen, amino or carboxy;
Ar$^1$ and Ar$^2$ are each independently pyridyl or substituted pyridyl;
X is selected from the group consisting of Cl, Br, I, —OSO$_2$—CF$_3$, and —OOC—CF$_3$.

14. The method of claim 9, wherein Ar$^1$ and Ar$^2$ are each independently pyridyl.

* * * * *